United States Patent [19]
Heitman

[11] Patent Number: 5,681,993
[45] Date of Patent: Oct. 28, 1997

[54] METHOD AND APPARATUS FOR MEASURING GRIP FORCE

[76] Inventor: Lynn Byron Heitman, 4711 Sycamore La., Parker, Tex. 75002

[21] Appl. No.: 229,174

[22] Filed: Apr. 18, 1994

[51] Int. Cl.⁶ .................................................. G01L 5/00
[52] U.S. Cl. ......................................... 73/379.02; 473/202
[58] Field of Search ............................. 73/379.02, 379.03; 273/187.5, 81 R, 165, 166, 81.5, 81 D; 482/49; 473/201, 202

[56] References Cited

U.S. PATENT DOCUMENTS

| | | | |
|---|---|---|---|
| 3,323,367 | 6/1967 | Searle | 273/187.5 |
| 3,647,504 | 3/1972 | Hayes, Jr. et al. | 117/36.7 |
| 3,670,574 | 6/1972 | Edwards | 73/379.02 |
| 3,762,720 | 10/1973 | Jett | 273/187.5 |
| 3,897,058 | 7/1975 | Koch | 273/187.5 |
| 4,104,910 | 8/1978 | Ogata et al. | 73/141 R |
| 4,138,118 | 2/1979 | Budney | 273/183 D |
| 4,488,726 | 12/1984 | Murray | 273/183 B |
| 4,861,034 | 8/1989 | Lee | 273/183 D |
| 5,221,088 | 6/1993 | McTeigue et al. | 73/379.02 |

FOREIGN PATENT DOCUMENTS

1587191  4/1981  United Kingdom ............ 273/187.5

Primary Examiner—Elizabeth L. Dougherty
Attorney, Agent, or Firm—Gregory M. Howison; Joseph Shallenberger

[57] ABSTRACT

A plurality of force sensors (20) are provided each having parameters and an output with the force sensors (20) disposed at specific predetermined pressure points between the human hand and an object to which a force is to be applied. A conversion device (28) is also provided for converting the outputs of the force sensors into outputs discernible to humans. The parameters of the force sensors vary proportionally with the amount of force applied to the force sensors (20). These force sensors (20) may be disposed in a substantially abutting relationship with the object to which the force is to be applied, the force sensors (20) may be disposed in substantially abutting relationship with the human hand, the force sensors (20) may be attached directly to the human hand or the object to which the force is to be applied or force sensors (50) and (52) may be attached to a glove (50) which fits over a portion of the human hand. The conversion device converts the outputs of the force sensors into audible sound frequencies which may vary in proportion to the force level and the location of the force into alphanumeric outputs proportional to the force level and location of the force or any other color or monochrome display that varies in relation to the proportion and level of the force. The conversion device may also convert the output of the force sensors to vibratory outputs or electrical stimulus currents that vary in proportion to the force level and location of the force.

37 Claims, 9 Drawing Sheets

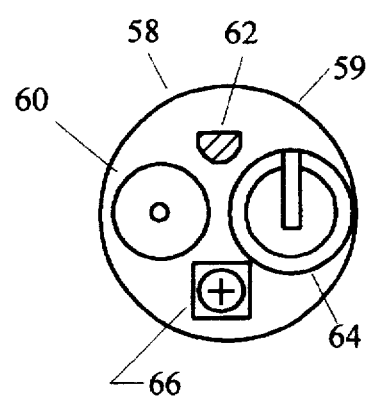
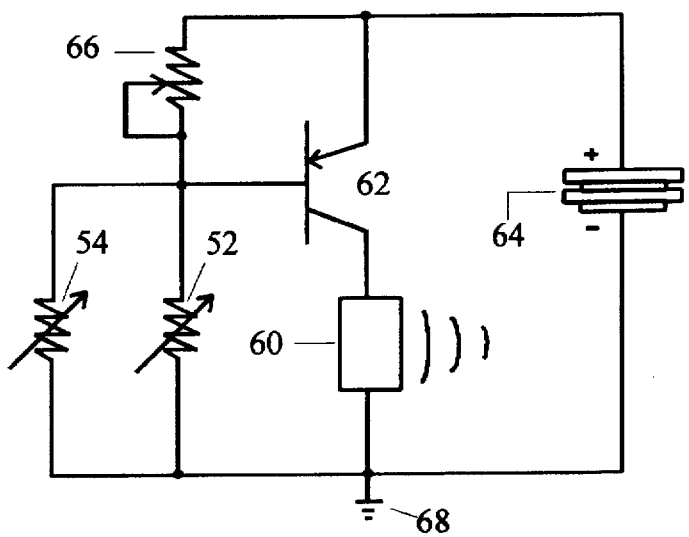
FIGURE 2C    FIGURE 2D

1

METHOD AND APPARATUS FOR MEASURING GRIP FORCE

BACKGROUND OF THE INVENTION

Measuring forces exerted on objects by the human hand is a complex and troublesome proposition. Since the hand is a complex mechanism, the actual forces generated by the hand are correspondingly complex and must be measured over a specific application area in order to provide any meaningful dam. Because of this, measuring the force applied to an object by the human hand is difficult and expensive to measure with any reasonable accuracy. In the past, this has not been attempted except by expensive and complicated machines for a very limited number of purposes. These machines were not very practical and could not be used in a wide variety of applications. When these machines were used on a specific application, the outputs of these machines were very difficult to interpret in a meaningful manner. A further problem with these machines was that they were not portable and could not be used by the mass public because of their cost, size and complexity.

SUMMARY OF THE INVENTION

The present invention disclosed and claimed herein comprises a device and a method for measuring force applied to an object by the human hand. A plurality of force sensors are provided each having an associated set of parameters and an output. The force sensors are disposed at specific predetermined pressure points between the human hand and an object to which a force is to be applied. A conversion device is also provided for converting the outputs of the force sensors into outputs discernible to humans. The parameters of the force sensors vary proportionally with the amount of force applied to the force sensors. These force sensors may be disposed in a substantially abutting relationship with the object to which the force is to be applied, they may be disposed in a substantially abutting relationship with the human hand, they may be attached directly to the human hand or the object to which the force is to be applied, or they may be attached to a glove which fits over a portion of the human hand. The conversion device converts the outputs of the force sensors into audible sound frequencies which may vary in proportion to the force level and the location of the force. Alternately, the outputs of the force sensors are converted into alphanumeric outputs proportional to the force level and location of the force, or any other color or monochrome display that varies in relation to the proportion and level of the force. The conversion device may also convert the output of the force sensors to vibratory outputs or electrical currents that vary in proportion to the force level and location of the force and produce a stimulus to the user's hand.

In another aspect of the present invention, a magnetic sensor is disposed proximate to the force sensors to interrupt the output of the sensors when the sensors are not proximate to the object to which the force is to be applied.

BRIEF DESCRIPTION OF THE DRAWINGS

For a more complete understanding of the present invention and the advantages thereof, reference is now made to the following description taken in conjunction with the accompanying Drawings in which.

2

Figure 2:
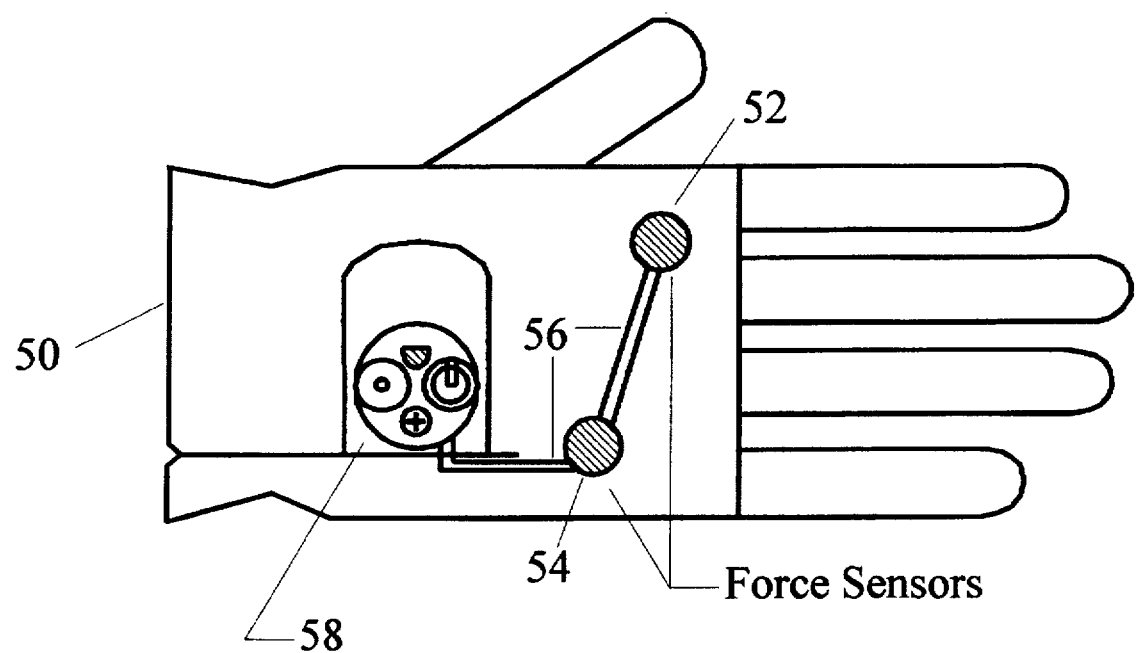
FIG. 2 illustrates a top view of the system of the present invention as applied to a golf glove.
Figure 2A:
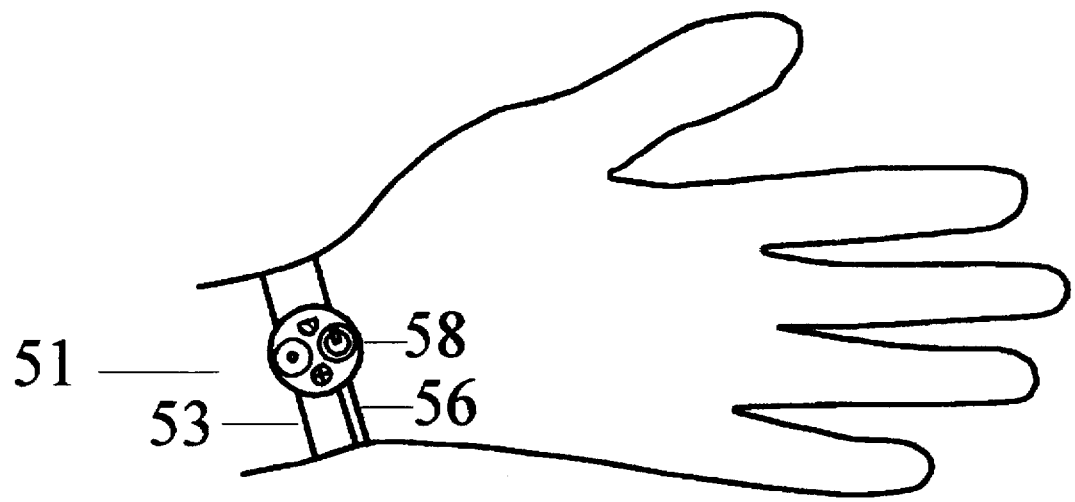
Figure 2B:
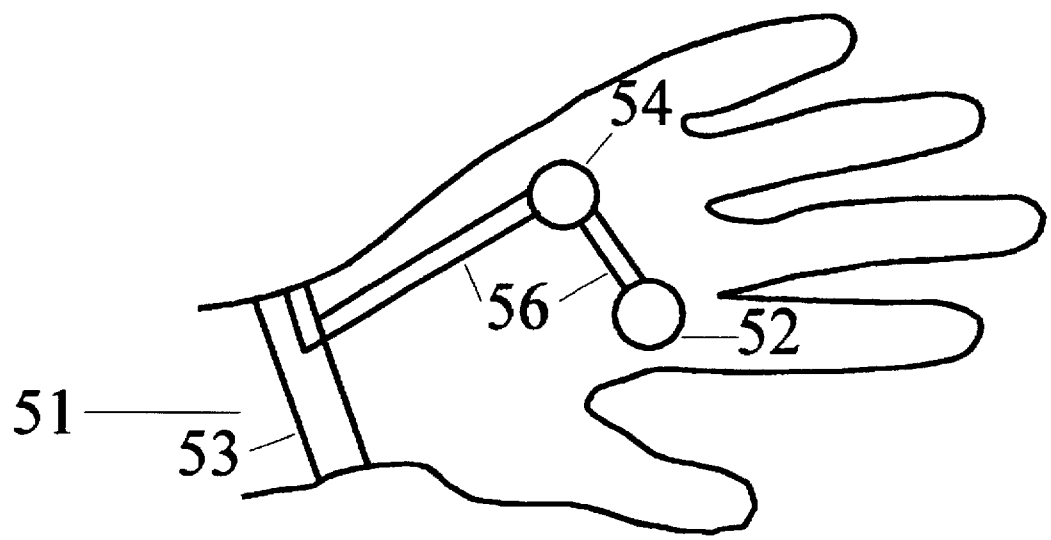
Figure 3:
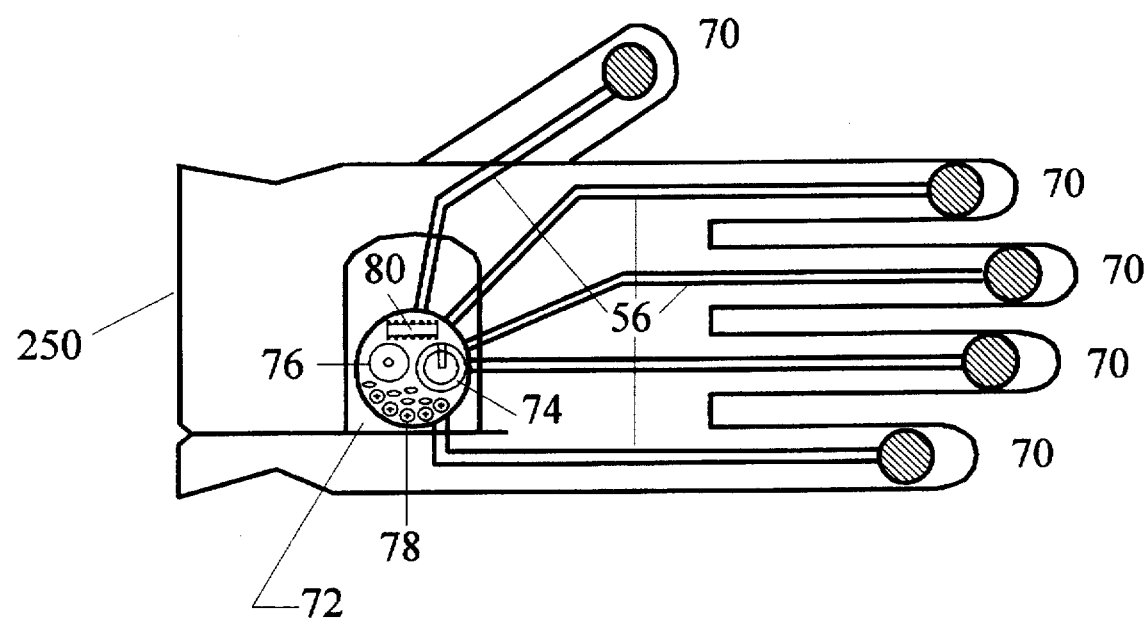
Figure 3A:
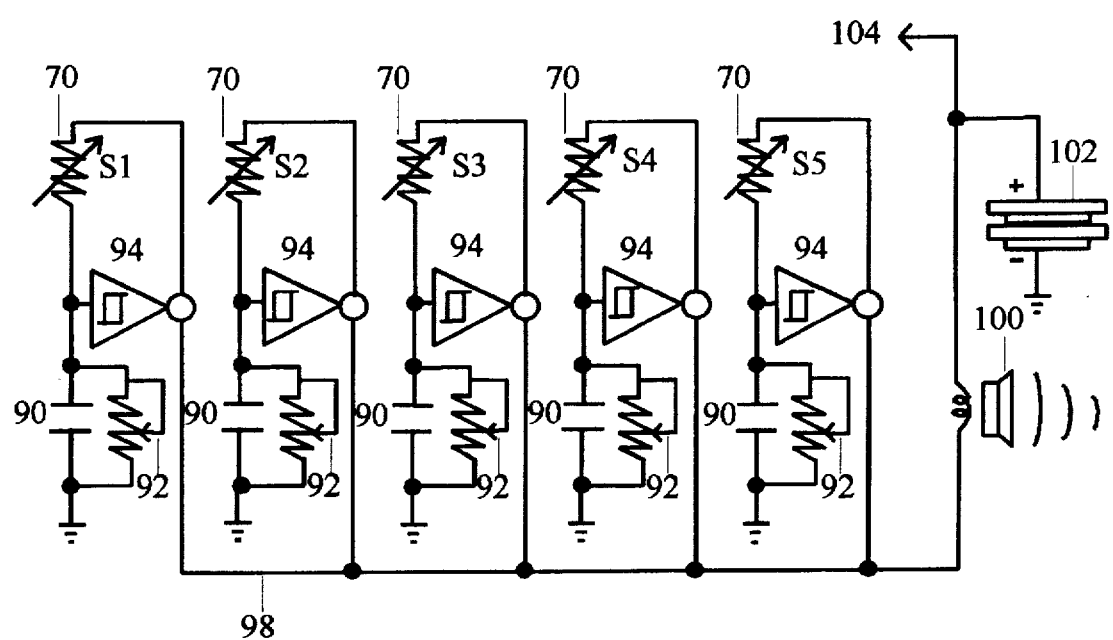
Figure 4A:
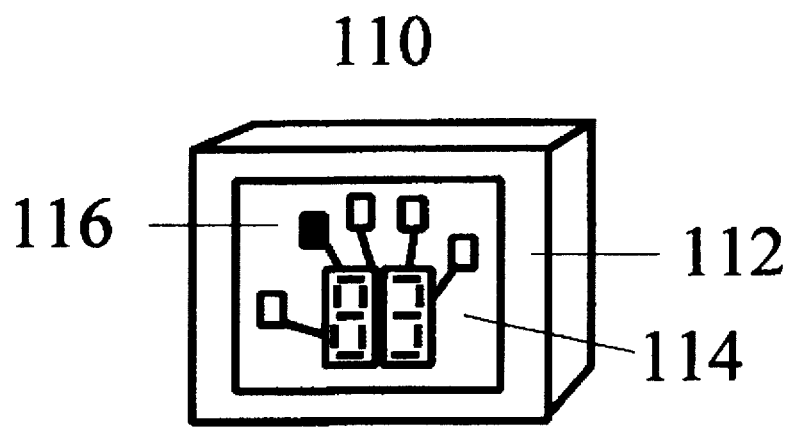
Figure 4B:
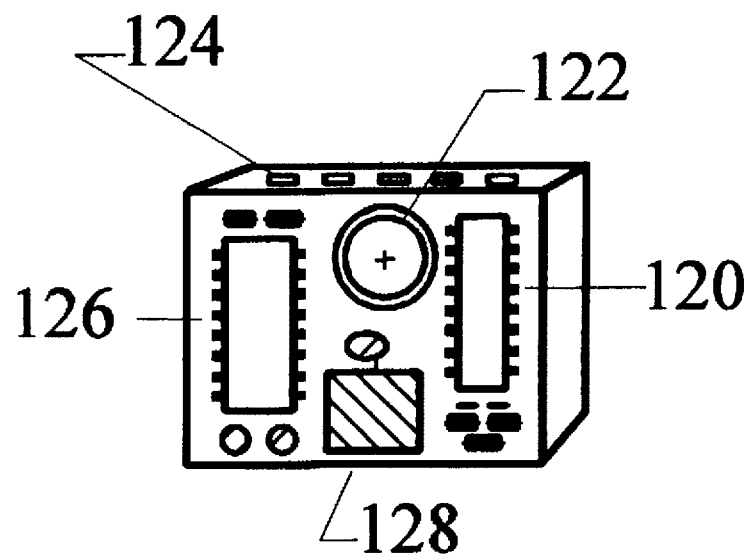
Figure 5:
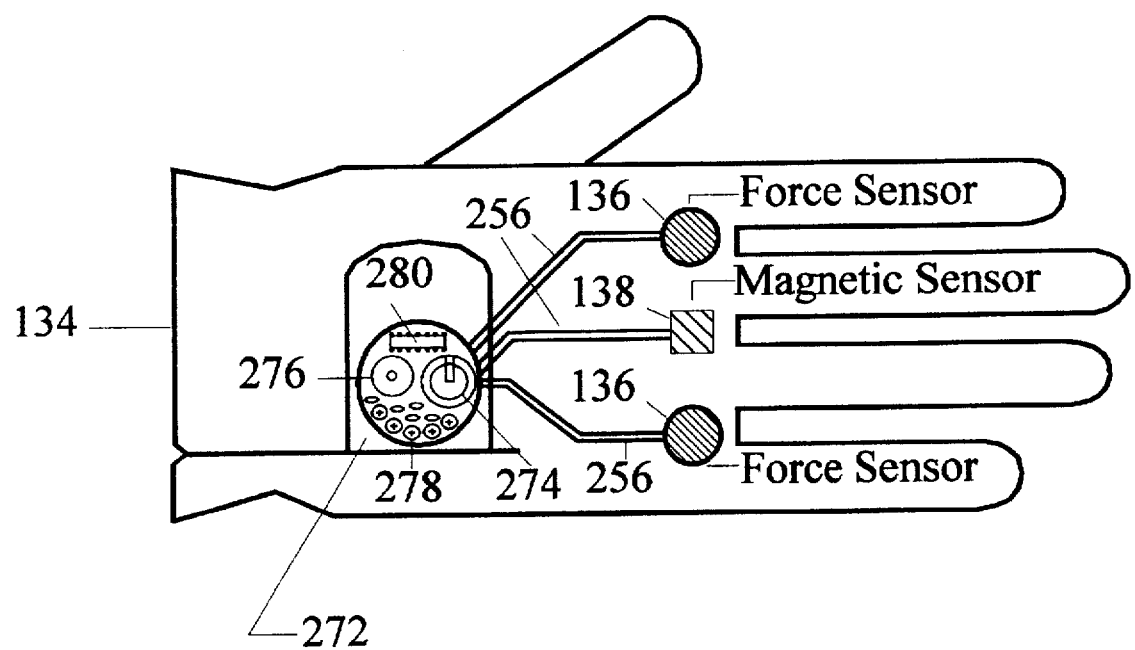
Figure 6:
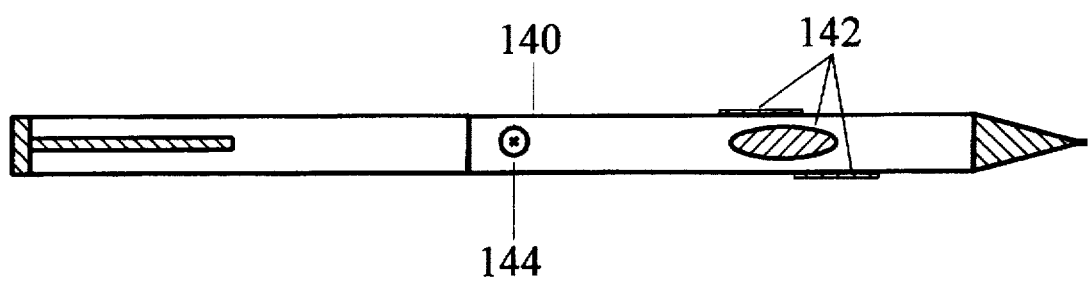

FIG. 2a illustrates a dorsal view of the human hand with sensors directly attached to the hand;

FIG. 2b illustrates a palmar view of the human hand illustrating the sensors directly attached thereto;

FIG. 2c illustrates a detailed top view of the electronics module;

FIG. 2d illustrates a schematic diagram of the electronics module;

FIG. 3 illustrates a top view of an alternate embodiment of the system of the present invention using a variable frequency implementation;

FIG. 3a illustrates a schematic view of the alternate embodiment of the present invention using a variable frequency implementation;

FIG. 4a illustrates a front view of an alternate embodiment of the output converter of the system of the present invention;

FIG. 4b illustrates a rear view of an alternate embodiment of the output converter of the system of the present invention;

FIG. 5 illustrates a top view of an alternate embodiment of the system of the present invention as applied to an aircraft pilot's gloves; and FIG. 6 illustrates a detailed top view of an alternate embodiment of a system of the present invention as applied to a writing instrument.

DETAILED DESCRIPTION OF THE INVENTION

Figure 1:
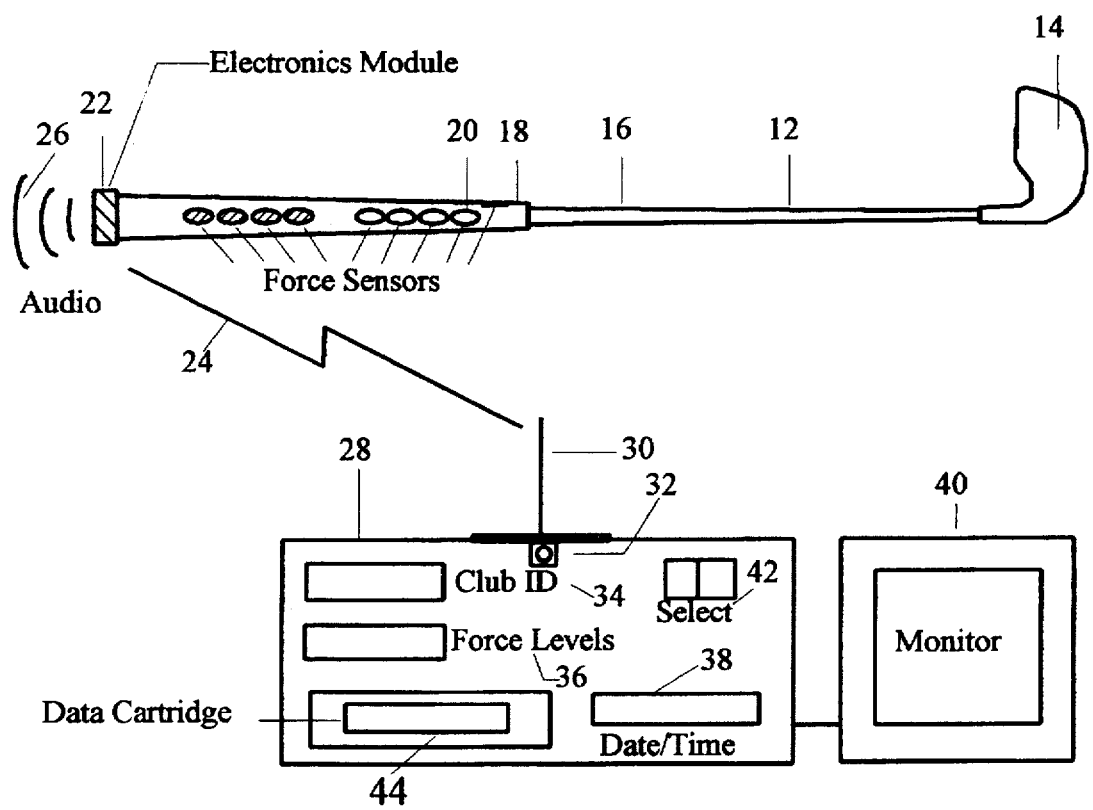
FIG. 1 illustrates a side elevational view of the system of the present invention as applied to a golf club.

Referring now to FIG. 1, there is illustrated a side elevational view of the system of the present invention as applied to a golf club. A golf club 12 is provided having a head 14, a shaft 16 and a grip 18. Force sensors 20 are placed either on top of or in the grip 18. The grip 18 may be of one piece construction or consist of a wrap which wraps around the golf club 12. The sensors 20 are placed on the golf club grip at identified points where the golfer places each hand. The force sensors 20 are placed at specific pressure points between the golfer's hand and the golf club grip 18. The force sensors' 20, resistance, capacitance, inductance or impedance vary proportionally with the amount of force applied to the force sensor 20. Specific markings or contoured shapes (not shown) can be used to identify the location of the force sensors 20. An electronic circuit (not shown) is connected to the force sensors 20 and mounted on the tip of the club handle 22. The electronic circuit (not shown) is used to transfer information received from the force sensors 20 to a remote location for display and analysis via a communication link 24 which could be comprised of an electrical or fiber optic cable, an RF link, an infrared system, or an ultrasonic communication link. The electronic circuit (not shown) can also produce audible tones 26, whose frequencies vary in proportion to the force supplied to the grip 18 and the force sensors 20 and to the location of the force.

Also shown in FIG. 1 is one embodiment of an output converter 28. The output converter 28 comprises an antenna 30 or an infrared sensor 32 to receive information from the electronic circuit of the golf club 12. The output converter 28 may contain various outputs such as one output 34 associated with the identity of the club used, an output 36 for the force level applied to the force sensor 20 and one output 38 for the date and time of the reading. A monitor 40 may also be connected to the output converter 28 for various visual and numerical outputs. A force sensor selector 42 is also provided to select the display from the various force sensors 20, as is a data cartridge 44 to record the outputs of the force sensors 20 and to input pre-recorded force sensor readings for comparison.

In operation, a golfer would grip the golf club 12, placing his hands on the grip 18 such that his fingers were placed over the force sensors 20. The force sensors 20 would then detect the force applied by the golfer's hand to the golf club 12 through the golf club grip 18. The electronic module (not shown) placed in the tip of the golf club 22 would then either convert the signals produced by the force sensors into an audible output 26 or transmit the information via electrical or fiber optic cable, radio, infrared, ultrasonic or any of the other available communication links 24 to an output converter 28. A person or persons at the location of the output converter 28 could tell what club was being used by the golfer by the indication of the club identification 34 and could tell what force level was being applied to the force sensors through the readout 36. The audible output 26 can be set to begin at a predetermined level prior to using the golf club 12. The monitor 40 can also be used to track the force applied to the force sensors 20 or to see when a predetermined force has been met upon each of the force sensors 20. The feedback provided by the output converter allows a golfer to learn how to place their hand on the golf club grip and how much force to apply at each location by applying the appropriate feedback at the club through comparison of the results with those previously recorded and stored at the output converter location. This comparison may be made by viewing the monitor 40 and using data input with the data cartridge 44. The monitor 40 may also be used to view a specific color or variable color, or a fixed or variable monochrome indicator which varies in proportion to the force supplied to the force sensors 20.

Referring now to FIG. 2, there is illustrated a top view of an alternate embodiment of the system of the present invention as applied to a golf glove 50. The golf glove 50 is made of any suitable material, such as leather, flannel or cloth. The golf glove 50 contains two force sensors 52 and 54, which are attached to the palm side of the glove at selected positions thereon. These force sensors are similar to the force sensors 20 described with respect to FIG. 1. Force sensor 52 is disposed at the head of the second metacarpus of the human hand. Force sensor 54 is disposed at the base of the fifth metacarpus of the human hand. The force sensors 52 and 54 are connected to an electronics module 58 by wires 56. An electronics module 58 is located on the upper dorsal surface of the golf glove 50. The force sensors 52 and 54 and the interconnecting conductors 56 are made of a flexible material such that they do not interfere with the feel and the use of the golf glove 50.

Referring now to FIG. 2a there is illustrated a dorsal view of a human hand 51 and in FIG. 2b there is illustrated a palmar view of the human hand 51, both illustrating an alternate embodiment of the system of the present invention. The electronics module 58 is held in place by a wrist band 53. The force sensors 54 and 52 in this embodiment are attached directly to the skin of the human hand 51 by a removable adhesive. The force sensors 54 and 52 are connected to the electronics module 58 by the interconnecting conductors 56 which are flexible.

Referring now to FIG. 2c, there is illustrated a detailed top view of the electronics module 58. The electronics module 58 consists of a rigid housing 59 containing a transducer 60, a transistor 62, batteries 64 and a potentiometer 66.

Referring now to FIG. 2d, there is illustrated a schematic diagram of the electronics module 58 applied to the present invention. A bipolar PNP transistor 62 is provided having the collector thereof connected to one end of a transducer 60, with the other end of the transducer 60 being connected to a ground 68. A battery 64 is provided having a positive and a negative side, the battery 64 comprising any type of portable battery, such as a lithium battery. The emitter of the transistor 62 is connected to the positive side of the battery 64. The negative side of battery 64 is connected to the ground node 68. A potentiometer 66 is provided having one side thereof connected to the positive side of the battery 64 and the other side thereof connected to the base of the transistor 62. Force sensors 52 and 54 are provided connected in parallel, with one side thereof connected to the base of the transistor 62 and the other side thereof connected to the ground node 68.

In operation, a golfer (not shown) would wear the golf glove 50. When the golfer (not shown) holds the golf club 12, the club 12 rests across the palm of the golf glove such that the sensors 52 and 54 are located between the golf glove 50 and the palm of the golfer's hand (not shown). When the golfer squeezes the golf club 12 and produces a certain force on the sensors 52 and 54, the transducer 60 is activated such that an audible sound is heard. The transducer 60 contains an integral driver that produces a fixed frequency audible tone to signal a golfer when the level of force being applied exceeds a selected level. The potentiometer 66 allows the golfer to adjust the force level required to activate the transducer 60. The force sensors 52 and 54 could also be set so that a tone is heard when the force exceeds a predetermined level, is less than a predetermined level, or is equal to a predetermined level. The device could also be set such that a tone is heard when the force on one sensor is greater or less than the force on another sensor or is equal to that on another sensor. It can also be set such that a tone is heard when the combined force of the two sensors meets, exceeds, or is less than the predetermined force. These audible tones could be useful for determining if the club 12 is being held correctly or if too much force is being applied to one portion of the club 12.

Referring now to FIG. 3, there is illustrated a top view of an alternate embodiment of the system of the present invention. The apparatus of FIG. 3 is basically that as shown in FIG. 2, with a variable frequency output provided for each sensor. A glove 250 is provided with force sensors 70, which are substantially similar to the force sensors 20 as described above disposed at the third row of phalanges of each finger and the thumb of the human hand. Each force sensor 70 is connected to an electronics module 72 by interconnecting conductors 56. An electronics module 72 is also provided that is similar to the electronics module 58, as described above with respect to FIG. 2, in that it contains a battery 74 and a transducer 76. The electronics module 72 contains five potentiometers 78, one for each force sensor 70. The electronics module 72 also contains an integrated circuit chip 80.

Referring now to FIG. 3a, there is illustrated a schematic diagram of the embodiment of FIG. 3. There are five capacitors 90 provided, each having one side thereof connected to ground. Connected in parallel across each capacitor 90 are five potentiometers 92, each having one side connected to ground and the other side thereof connected to the other side of the respective capacitor 90. The other side of each of the capacitors 90 is connected to the input of a hex inverter with a Schmidt trigger 94. The inverter 94 makes use of a transistor/transistor logic (TTL) circuitry. Connected between the input and output of each hex inverter 94 is a force sensor 70 substantially similar to force sensors 20 illustrated in FIG. 1. The output of each inverter 94 is connected to a common node 98. Also connected to node 98 is one side of a transducer 100, substantially similar to the transducer 60 described hereinabove with respect to FIG. 2. A battery 102 has the negative terminal thereof connected to ground and the positive terminal thereof connected to the other side of transducer 100 and to a supply node 104, which supply node 104 is connected to the supply input of each inverter 94.

In operation, each sensor 70, capacitor 90 and inverter 94 configuration creates an independent oscillator whose frequency varies with the level of force applied to the sensor 70. At low force levels, the sensor 70 resistance is very high, the feedback is very small and the oscillator does not run. As more force is applied, the resistance is reduced and the oscillator begins to oscillate, the frequency increasing with increasing force. A potentiometer 92 is connected across each capacitor 90 to control the minimum force level that will cause oscillation. This potentiometer 92 sets the desired force level for each sensor 70. The capacitor value is chosen to create a clearly discernible value for each sensor 70. All the oscillator outputs are logically wired to form a composite signal which is used to drive the transducer 100. The transducer 100 is a magnetic-coupled piezo device and contains a loudness control implemented as a movable mechanical baffle.

To calibrate the variable frequency glove 250, the user initially applies a force to one sensor 70 and then adjusts the associated potentiometer 92 so that the oscillation stops at the desired force level. The same adjustment is repeated for each force sensor 70. Sequentially pressing each force sensor 70 teaches the user the frequency associated with each force sensor 70. If the user exceeds the force on one or more of the sensors 70, the composite output of all the oscillators is audibly reproduced. The user then reduces the force on all of the force sensors 70 and then sequentially steps through each one again to learn the proper force to apply to each sensor 70. The user can then tell by the oscillation heard whether there is too much or too little force at each force sensor 96 and can adjust the force applied to such force sensors. The user can have more specific force levels monitored at each force sensor 70 by listening and remembering the frequencies that are output by the transducer 100.

Referring now to FIG. 4a, there is illustrated a front view of an LCD display and the vibration transducer used as an output converter for the variable frequency implementation described in FIG. 3. A housing 110 is provided with an LCD display 112 disposed on the front of the housing 110. The LCD display 112 consists of a force level numeric display 114 and a force sensor indicator 116. On the back of the module, an integrated circuit chip 120 containing the logic circuit is provided. Also provided are the batteries 122, connectors 124 to connect the module to the force sensors (not shown), an LCD driver 126 to drive the LCD display 112 and a motor and counterweight 128 to provide vibratory output.

In operation, the LCD vibrator module operates with circuitry similar to that shown and described in FIG. 3a with the exception that the transducer 100 is replaced by a motor and counterweight 128 to provide vibration which may be felt by the user. Also, an LCD driver 126 is provided to give a numeric force level display 114 and a force sensor indicator 116. The force level indicator 114 provides a numeric representation of the force, and a sensor indicator 116 indicates which sensors, if any, include the desired force level. Also, when any of the force levels exceed the desired force level, a vibration transducer consisting of a motor and counterweight 128 begins operation such that the user may feel the vibration and know that one of the force levels has been exceeded.

Referring now to FIG. 5, there is illustrated an alternate embodiment of the invention as applied to a glove 134 such as one an aircraft pilot might wear. The glove 134 is fabricated of flexible material such as that used in the glove worn by aircraft pilots. Force sensors 136 are provided on the glove and are placed such that they correspond to the heads of the second through the fifth metacarpi of the human hand. An electronics module 272 is also provided. Within the electronics module 272 is an integrated circuit chip 280, a transducer 276, battery 274 and potentiometers 278, the number of which correspond to the number of force sensors 136. The force sensors 136 are connected to electronics module 272 by interconnecting conductors 256 which are flexible so as not to interfere with the movement of the hand. The force sensors 136 are substantially similar to the force sensors 20 described with respect to FIG. 1 and the electronics in the electronics module 272 are substantially similar to that shown in FIG. 3 described above. The circuitry is substantially similar to that shown in FIG. 3a described above. In addition, there is provided a magnetic sensor 138 which is connected to the electronics module 272 by an interconnecting conductor 256.

In operation, the glove 134 in FIG. 5 works in a substantially similar way to that shown in FIG. 3 described above. The force sensors 146 are placed in relation to the palm of the hand to conform with the shape of a grip control stick used to fly certain airplanes. A pilot, (not shown), would wear the glove 134. When the pilot (not shown) holds an aircraft control stick (not shown), the control stick rests across the force sensors 136 such that the sensors 136 are located between the glove 134 and the palm of the pilot's hand (not shown). When the pilot's hand is in proximity with the aircraft control stick (not shown) the magnetic sensor 138 switches on the electronics module 272. When the pilot squeezes the control stick (not shown) and produces a certain force on the sensors 136, the transducer 276 is activated such that an audible sound is heard. The transducer 276 contains an integral driver that produces a fixed frequency audible tone to signal a pilot when the level of force being applied exceeds or falls below a selected level. The potentiometer 278 allows the pilot to adjust the force level required to activate the transducer 276. The force sensors 136 could also be set so that a tone is heard when the force exceeds a predetermined level, when the force is less than a predetermined level, or when the force is equal to a predetermined level. The device could also be set such that a tone is heard when the force on one sensor is greater or less than the force on another sensor or is equal to that on another sensor. It can also be set such that a tone is heard when the combined force of the two sensors meets, exceeds, or is less than the predetermined force. These audible tones could be useful for determining if the control stick is being held correctly or if too much or too little force is being applied to one portion of the control stick. Once the glove is calibrated, as described with respect to FIG. 3, the gloves emit a warning tone when the force levels are below, above or at a normal level and, thus, can be used to monitor the user's level of concentration. The magnetic sensor 138 is used to mute the sound output when the gloves 134 are not proximal to the magnetic control stick (not shown). This causes the glove not to produce an audible output when it is not in use controlling an aircraft.

Referring now to FIG. 6, there is shown a top view of a specially equipped writing instrument 140. Force sensors 142 are provided at the places on the writing instrument 140 where the fingers of the human hand would touch the writing instrument 140 when it is held correctly. An LED 144 is also provided. The electronics (not shown) are substantially similar to those shown and described above in FIG. 3 and FIG. 3a, with the exception that the output instead of being a transducer is the LED 144.

In operation, the force sensors 142 are located where the fingertips of the human hand would hold the writing instrument 140 when the writing instrument 140 is held correctly. The electronics (not shown) are located within the body of the writing instrument 140. The LED 144 would light up when the writing instrument 140 is held in an incorrect location or with an improper force placed on the force sensors 142. This device could be used by beginning students to teach the proper level of force and the proper grip used to hold and use a writing instrument such as that of 140.

In summary, there has been provided a device and a method for measuring force applied to an object by the human hand. A plurality of force sensors are provided each having parameters and an output with the force sensors disposed at specific predetermined pressure points between the human hand and an object to which a force is to be applied. A conversion device is also provided for converting the outputs of the force sensors into outputs discernible to humans. The parameters of the force sensors vary proportionally with the mount of force applied to the force sensors. These force sensors may be disposed in a substantially abutting relationship with the object to which the force is to be applied, the force sensors may be disposed in substantially abutting relationship with the human hand, the force sensors may be attached directly to the human hand or to the object to which the force is to be applied, or the force sensors may be attached to a glove which fits over a portion of the human hand. The conversion device converts the outputs of the force sensors into audible sound frequencies which may vary in proportion to the force level and the location of the force into alphanumeric outputs proportional to the force level and location of the force or any other color or monochrome display that varies in relation to the proportion and level of the force. The conversion device may also convert the output of the force sensors to vibratory outputs or electrical currents that vary in proportion to the force level and location of the force and produce a stimulus to the user's hand.

Although the preferred embodiment has been described in detail, it should be understood that various changes, substitutions and alterations can be made therein without departing from the spirit and scope of the invention as defined by the appended claims.

What is claimed is:

1. A method for measuring grip force on an object by the human hand which object is capable of moving relative to the user's head during use by the user, comprising the steps of:

providing a plurality of force sensors each sized for sensing an applied force in a localized area and providing an output signal, each sensor having associated therewith operating parameters, which operating parameters define how the output signal varies in relation to the force which is applied, the associated operating parameters of the force sensors varying proportionally with the amount of force applied to the sensor;

disposing the force sensors in a distributed manner between the human hand and the object to be gripped, the force sensors disposed in limited cross-sectional areas that correspond to the pressure points on the hand which produce substantially optimal performance results between the hand and the object to be gripped;

gripping the object with the human hand with the force sensors disposed therebetween; and converting the outputs of the force sensors into a single discernible output using a local processor and a local output system directly connected to the force sensors, the discernible output comprising a weighted average of the outputs of all of the sensors, the local output system directing the discernible outputs to the user from the object while the object is moving, such that the user can discern the location of the object during movement thereof for all positions of the object relative to the user's head during movement of the object.

2. The method of claim 1 and further comprising the step of disposing the force, sensors in substantial contact with the object to be gripped.

3. The method of claim 1 wherein the step of disposing the force sensors further comprises disposing the force sensors in contact with the human hand.

4. The method of claim 3 wherein the step of disposing the force sensors further comprises attaching the force sensors to a glove which fits over a portion of the human hand.

5. The method of claim 3 wherein the step of disposing the force sensors further comprises attaching the force sensors directly to the human hand.

6. The method of claim 3 wherein the force sensors are disposed at the base of the fifth metacarpus of the human hand and at the head of the second metacarpus of the human hand.

7. The method of claim 3 wherein said force sensors are disposed in a row across the heads of the second through the fifth metacarpi of the human hand.

8. The method of claim 3 wherein the force sensors are disposed at the third row phalanges of the human hand.

9. The method of claim 3 and further comprising the step of placing a magnetic sensor proximate to the force sensors such that movement of the force sensors results in movement of the magnetic sensor, and interrupting the output signal from the force sensors when the force sensors are moved away from the object.

10. The method of claim 1 wherein the step of disposing the force sensors comprises attaching the force sensors to a grip to be placed over the object to be gripped.

11. The method of claim 1 wherein the step of converting the outputs of the force sensors into discernible outputs comprises converting the outputs of the force sensors into audible sound frequencies at specific and adjustable force levels and locations.

12. The method of claim 1 wherein the step of converting the outputs of the force sensors into discernible outputs comprises converting the outputs of the force sensors into an audible sound frequency that varies in proportion to the force level and location of the force.

13. The method of claim 1 wherein the step of converting the outputs of the force sensors into discernible outputs comprises converting the outputs of the force sensors into alphanumeric outputs proportional to the force level and location of the force.

14. The method of claim 1 wherein the step of converting the outputs of the force sensors into discernible outputs comprises converting the outputs of the force sensors into a color display that varies in proportion to the force level and location of the force.

15. The method of claim 1 wherein the step of converting the outputs of the force sensors into discernible outputs comprises converting the outputs of the force sensors into a monochrome indicator display that varies in proportion to the force level and location of the force.

16. The method of claim 1 wherein the step of converting the outputs of the force sensors into discernible outputs comprises converting outputs of the force sensors into vibratory outputs that vary in proportion to the force level and location of the force.

17. The method of claim 1 wherein the discernable outputs comprise a single output, and further comprising, the step of averaging the outputs of the force sensors before the step of converting.

18. The method of claim 1 wherein the step of converting the outputs of the force sensors into discernible outputs comprises converting outputs of the force sensors into electrical currents that vary in proportion to the force level and location of the force and produce a stimulus in the user's hand.

19. A method for measuring grip force on an object by the human hand which object is capable of moving relative to the user's head during use by the user, comprising the steps of:
    providing a plurality of force sensors each sized for sensing an applied force in a localized area and providing an output signal, each sensor having associated therewith operating parameters, which operating parameters define how the output signal varies in relation to the force which is applied, the associated operating parameters of the force sensors varying proportionally with the amount of force applied to the sensor;
    disposing the force sensors in a distributed manner between the human hand and the object to be gripped, the force sensors disposed in limited cross-sectional areas that correspond to the pressure points on the hand which produce substantially optimal performance results between the hand and the object to be gripped;
    gripping the object with the human hand with the force sensors disposed therebetween;
    converting the outputs of the force sensors into a single discernible output using a local processor and a local output system directly connected to the force sensors, the discernible output comprising a weighted average of the outputs of all of the sensors, the local output system directing the discernible outputs to the user from the object while the object is moving, such that the user can discern the location of the object during movement thereof for all positions of the object relative to the user's head during movement of the object; and
    attaching the force sensors to a wrap and wrapping the wrap around the object to be gripped.

20. A device for measuring grip force on an object by the human hand which object is capable of moving relative to the user's head during use by the user, comprising:
    a plurality of force sensors each sized for and operable for sensing an applied force in a localized area and providing an output signal, each sensor having associated therewith operating parameters, which operating parameters define how the output signal varies in relation to the force which is applied, wherein said associated operating parameters of said force sensors vary proportionally with the amount of force applied to said force sensors, each of said force sensors disposed in a distributed manner and in limited cross-sectional areas that correspond to the pressure points on the hand which produce optimal performance results between said human hand and said object to be gripped; and
    a local conversion device which is directly connected to said force sensors for converting said output signals of said force sensors into a discernible output and as a local output system for outputting said discernible output from a point proximate the object for all positions thereof, the discernible output comprising a weighted average of the outputs of all of said force sensors, the local output system directing the discernible output to the user from the object while the object is moving, said conversion device converts said outputs of said force sensors into electrical currents that vary in proportion to the force level and location of the force and produce a stimulus in the user's hand, such that the user can discern the location of the object during movement thereof for all positions of the object relative to the user's head during movement of the object.

21. The device of claim 20 wherein said force sensors are disposed in contact with the object to be gripped.

22. The device of claim 20 wherein said force sensors are disposed in substantial contact with said human hand.

23. The device of claim 22 wherein said force sensors are attached to a glove which fits over a portion of said human hand.

24. The device of claim 22 wherein said force sensors are attached directly to said human hand.

25. The device of claim 22 wherein said force sensors are disposed at the base of the fifth metacarpus of the human hand and at the head of the second metacarpus of the human hand.

26. The device of claim 22 wherein said force sensors are disposed in a row across the heads of the second through the fifth metacarpi of the human hand.

27. The device of claim 22 wherein said force sensors are disposed in a row across the base of the first row of the second to the fifth phalanges.

28. The device of claim 20 and further comprising a magnetic sensor disposed proximate to the force sensors to interrupt the output of the force sensors when the force sensors are not proximal to the object.

29. The device of claim 20 wherein said force sensors are attached to a wrap wrapped around the object to be gripped.

30. The device of claim 20 wherein said force sensors are attached to a grip to be placed over the object to be gripped.

31. The device of claim 20 wherein said conversion device converts said outputs of the force sensors into audible sound frequencies at specific and adjustable force levels and locations.

32. The device of claim 20 wherein said conversion device converts said outputs of said force sensors into an audible sound frequency that varies in proportion to the force level and location of the force.

33. The device of claim 20 wherein said conversion device converts said outputs of said force sensors into alphanumeric outputs proportional to the force level and location of the force.

34. The device of claim 20 wherein said conversion device converts said outputs of said force sensors into a color display that varies in proportion to the force level and location of the force.

35. The device of claim 20 wherein said conversion device converts said outputs of said force sensors into a monochrome indicator display that varies in proportion to the force level and location of the force.

36. The device of claim 20 wherein said conversion device converts said outputs of said force sensors into vibratory outputs that vary in proportion to the force level and location of the force.

37. A device for measuring grip force on an object by the human hand which object is capable of moving relative to the user's head during use by the user, comprising:

a plurality of force sensors each for sensing an applied force and providing an output signal, each having associated therewith operating parameters which operating parameters define how the output signal varies in relation to the force which is applied, each of said force sensors disposed in a distributed manner and in limited cross-sectional areas that correspond to the pressure points on the hand which produce optimal performance results between said human hand and said object to be gripped; and a local conversion device which is directly connected to said force sensors for converting said output signals of said force sensors into a discernible output and a local output system for outputting said discernible output from a point proximate the object for all positions thereof, the discernible output comprising a weighted average of the outputs of all of said force sensors, the local output system directing the discernible output to the user from the object while the object is moving, such that the user can discern the location of the object during movement thereof for all positions of the object relative to the user's head during movement of the object, wherein the discernable outputs comprise a single output, and further comprising an averaging device connected between said force sensor and said local conversion device operable to average said output signals of said force sensors.

* * * * *